United States Patent [19]

Hedberg et al.

[11] Patent Number: 5,740,811
[45] Date of Patent: Apr. 21, 1998

[54] DEVICE AND METHOD FOR GENERATING A SYNTHESIZED ECG

[75] Inventors: Sven-Erik Hedberg, Kungsängen; Jakub Hirschberg, Täby, both of Sweden

[73] Assignee: Pacesetter AB, Solna, Sweden

[21] Appl. No.: 756,374

[22] Filed: Nov. 26, 1996

[30] Foreign Application Priority Data

Nov. 28, 1995 [SE] Sweden .................. 9504258

[51] Int. Cl.$^6$ .................. A61N 1/37; A61B 5/0402
[52] U.S. Cl. .................. 128/697; 607/27
[58] Field of Search .................. 607/9, 27; 128/696, 128/697, 699

[56] References Cited

U.S. PATENT DOCUMENTS

| | | |
|---|---|---|
| 4,870,974 | 10/1989 | Wang . |
| 5,231,990 | 8/1993 | Gauglitz .................. 128/697 |
| 5,313,953 | 5/1994 | Yomtov et al. .................. 128/696 |
| 5,331,966 | 7/1994 | Bennett et al. .................. 128/696 |
| 5,404,877 | 4/1995 | Nolan et al. . |
| 5,425,373 | 6/1995 | Causey et al. .................. 128/697 |
| 5,497,780 | 3/1996 | Zehender .................. 128/696 |

FOREIGN PATENT DOCUMENTS

| | | |
|---|---|---|
| 0 310 216 | 4/1989 | European Pat. Off. . |
| 0 443 496 | 8/1991 | European Pat. Off. . |
| 0 465 241 | 1/1992 | European Pat. Off. . |
| 0 596 319 | 5/1994 | European Pat. Off. . |
| 0 605 244 | 7/1994 | European Pat. Off. . |
| 4307545 | 9/1994 | Germany .................. 128/697 |
| WO 92/02171 | 2/1992 | WIPO . |

*Primary Examiner*—William E. Kamm
*Assistant Examiner*—George R. Evanisko

[57] ABSTRACT

In a method and apparatus for physiological signal processing, a number of measured physiological signals are obtained in vivo from a subject and at least one of these measured physiological signals is supplied to the input of each first signal processing unit in a group of first signal processing units. Within each signal processing unit, the physiological measurement signal (or signals) supplied thereto is/are subjected to at least one transfer function so as to produce a pre-treated signal at the output of that first signal processing unit. The pre-treated signals from all of the first signal processing units are combined in a second signal processing unit so as to produce at least one synthesized ECG signal.

25 Claims, 11 Drawing Sheets

DEVICE AND METHOD FOR GENERATING A SYNTHESIZED ECG

BACKGROUND OF THE INVENTION

1. The Field of the Invention

The invention relates to a device and a method for signal processing known intracardiac signals obtained from electrodes in an implantable heart stimulator/defibrillator/monitoring system (an active implanted system) and a method for use of detected intracorporal cardiac signals and also to an active implant including such a device in whole or in part.

2. Description of Related Art

Today an ECG is recorded by applying electrodes (limb and chest electrodes) on the outside of the body at specific points and subsequently registering electrical activity in the heart. Since the signals have to pass through tissue, muscles, bone and adipose tissue the signals are partly disguised and also the muscles in themselves display electrical activity which may hide or distort the signals from the heart.

A complementary measure to the ECG is to transmit signals by telemetry from intracardial electrodes in the form of an IEGM, an intracardiac electrogram. This may be done e.g. in follow-ups after implantation and when possibly adjustment of controlling parameters in the active implant occurs. The IEGM is usually combined by the practitioner with the measuring of a surface ECG.

Measuring signals obtained from implanted electrodes is known within the art. A method and an apparatus for detection of ECG and/or blood pressure (BP) waveforms and measuring of the R—R and Q–T intervals from the detected ECG signals so as to determine the pulse rate and to stimulate the heart is described in U.S. Pat. No. 4,870,974.

The purpose of this method is to derive the VFT (Ventricular Fibrillation Threshold) indirectly from measurements of the PVCT (Premature Ventricular Contraction Threshold), NET (Multiple Extrasystole Threshold), and VTT (Ventricular Tachycardia Threshold). Stimulation pulses for the stimulation of the heart are generated, as well as pulse trains intended to cause the above phenomena. The threshold is detected by incrementally giving the pulse trains a higher amplitude. The ECG disclosed in this publication is measured by extracorporeal means, i.e., by surface measurements, while the stimulation pulses and the pulse trains are applied via either a cardiac catheter or in the esophagus.

A method and an implantable pacemaker suited for bradyarrhythmia therapy which stimulates and senses and obtains the ECG signal from the by stimulation evoked response in the heart, i.e. the QRS complex, is described in European Application 605 244. The problem described therein is that of the large residual potential which remains across the bipolar electrodes. This problem is solved by processing the signals sensed by the ring and tip electrode of a typical pacemaker bipolar lead. The circuit senses each of these signals from the ring and tip electrodes in a unipolar mode. The sensed electrical signals are subsequently added to cancel or nullify the opposing residual potentials which remain on the ring and tip electrode post pacing. The common-potential ECG signal is added and presented for subsequent detection of the QRS complex. In this way the higher residual potential signals are removed prior to the subsequent signal processing and the low level ECG signal is retained. This is thus an adding procedure and is not a processing of the signals in a differential mode.

Another example of combinations of signals and the use of time of incidence for acceptance of true atrial events by combining signals from different electrodes and using a logic unit is described in European Application O 596 319 in which a heart stimulator is described having a pulse generator and an electrode system which contains at least one bipolar electrode with one electrode arranged in the atrium and one electrode in the ventricle respectively, for detection of atrial and ventricular activity.

SUMMARY OF THE INVENTION

An object of the invention is to provide, from the implanted electrodes of an active implant (pacer and/or a defibrillator and/or implanted monitoring systems), a type of ECG which in appearance can be substituted for a surface ECG and which may be used especially postoperatively and for follow-ups (repeated) after the implantation of a stimulator or the like or for, e.g., checking the functioning of such a stimulator or for adjusting the parameters controlling the active implant whenever a programmer is in communication with the active implant.

Another object is to provide easier and faster follow-ups after an implantation without the use of additional extracorporeal electrodes.

Another object is to allow signals to be transmitted over public telephone lines for use by the practitioner for follow-ups and for diagnostic use by the practitioner located away from the patient having the active implant. Also, an object is to synthesize a surface ECG so that the practitioner will recognize the signals and be able to interpret the signals with his/her knowledge of a conventionally obtained surface ECG.

Another object of the invention is to make use of the signals from each electrode and to be able to exclude and/or lessen the effects of the information in the signal of electrical activity in the very close proximity to the electrode.

Yet another object is to be able to better distinguish between paced and spontaneous heart activities such as: capture, inhibition, fusion beats, etc.

A further object is to provide a diagnosis means to be used in diagnosing and detection of ischemia and in resolving which type of tachycardia is present in tachycardia cases. The indications of ischemia in the heart shown by the implanted electrodes should be easier to detect and also to counteract via the pacing of the heart. This can be the earliest warning that can be seen of ischemia or other heart diseases.

Still another object is to provide means for registering changes in the ECG in a person having an active implant, which changes will constitute contraindications or indications for adjustment of the rate responsive function in which case the rate will remain unchanged or adjusted in some other way indicated by analysis of the recorded ECG.

The above object is achieved in accordance with the principles of the present invention in a signal processing device, a medical stimulation system, and a method, wherein measured signals from two or more intracardiac and/or extracardiac electrodes are combined and a synthesized surface ECG is obtained by subjecting the measured signals to signal processing. The term "synthesized ECG" as used herein means a signal generated from at least two in vivo signals, such as at least two IEGMs, which provides the same information as a standard surface ECG.

In the embodiment of the invention directed to a cardiac stimulation system, the components which generate the synthesized ECG can be completely contained within an implantable unit, such as a pacemaker, cardioverter or defibrillator, or the measured signals can be obtained by an implanted unit and the information telemetered to an extracorporeal unit, with the signal processing to produce the synthesized ECG taking place in an extraporal unit. The extracorporeal unit in which the signal processing takes place need not necessarily be disposed near the patient. The measured signals can be extracorporeal telemetered to a unit which can then transmit the signals, for example by conventional telephone lines, to a remote location at which a physician, equipped with the extracorporeal signal processor, can then generate the synthesized ECGM and analyze it.

Signal processing takes place in accordance with the invention by individually subjecting at least two of the signals measured across respective pairs of the electrodes to a transfer function, thereby obtaining at least two pre-treated signals, and these at least two pre-treated signals are then combined to form at least one synthesized ECG.

According to the invention, it has been surprisingly found that by interconnecting two or more intracardiac and/or extracardiac electrodes—electrically connecting the electrodes measuring signals from these electrodes, and thereafter subjecting these signals to signal processing, a synthesized surface ECG may be obtained. This signal processing may be undertaken in a neural network and/or using fuzzy logic, and/or with a summation of processed signals.

According to the invention it has been shown that IEGM recordings between different electrodes in defibrillation and pacing systems show similarities to a conventionally obtained surface ECG. The inventive method is to measure signals between at least two groups of interconnected electrodes, where each group contains signals from at least one electrode.

According to the invention only electrodes implanted in the heart and/or implanted intra-corporal electrodes belonging to an active implant are used to create, from measurements of electrical activity in the heart and signal processing, a synthesized ECG which gives the same or other information as the standard surface ECG.

Another problem which is solved by the invention is that placing electrodes on the patient's surface and connecting these to the ECG machine no longer will be necessary since the signals from the implanted electrodes may be sensed using telemetry. This creates the possibility to relay these signals, even by telephone, from the patient to the physician, who may make a printout of the signals and analyze the ECG.

BRIEF DESCRIPTION OF THE DRAWINGS

FIG. 5b shows the influence of a nonlinear amplification (transfer function) on the same signals as in FIG. 5a.

DESCRIPTION OF THE PREFERRED EMBODIMENTS

Figure 1:
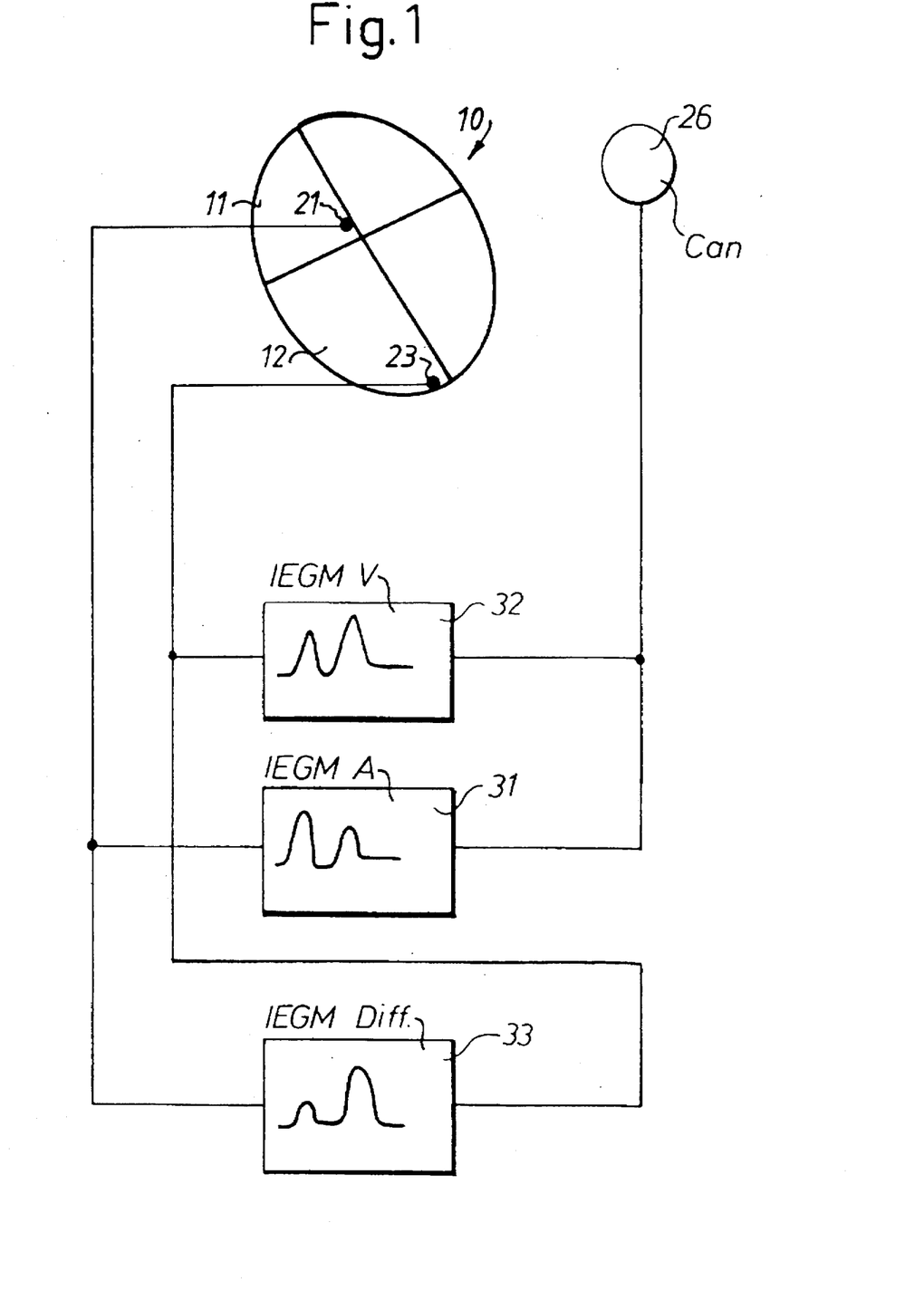
FIG. 1 is a schematic representation of an electrode configuration used in an active implant system (DDD,VDD) according to the prior art, using unipolar electrodes, which may be used in accordance with the invention.

For assistance in explaining the invention, FIG. 1 schematically shows a known electrode configuration for registering IEGMs (intracardiac electrograms) between different implanted electrodes, suitable for use in the inventive stimulator or diagnostic device. FIG. 1 shows a heart 10 with two implanted unipolar electrodes 21 and 23 in the atrium 11 and in the ventricle 12, respectively. Also shown is an extracardiac electrode 26, which may be the housing of the stimulator (can). Signals are measured between the can and electrodes 21 and 23, producing an atrial IEGM A in unit 31 and a ventricular IEGM V in unit 32. The differential signal between the two electrodes 21 and 23 produces a differential signal in unit 33. Units 31, 32, and 33 are the monitoring units for the IEGMS.

Figure 2:
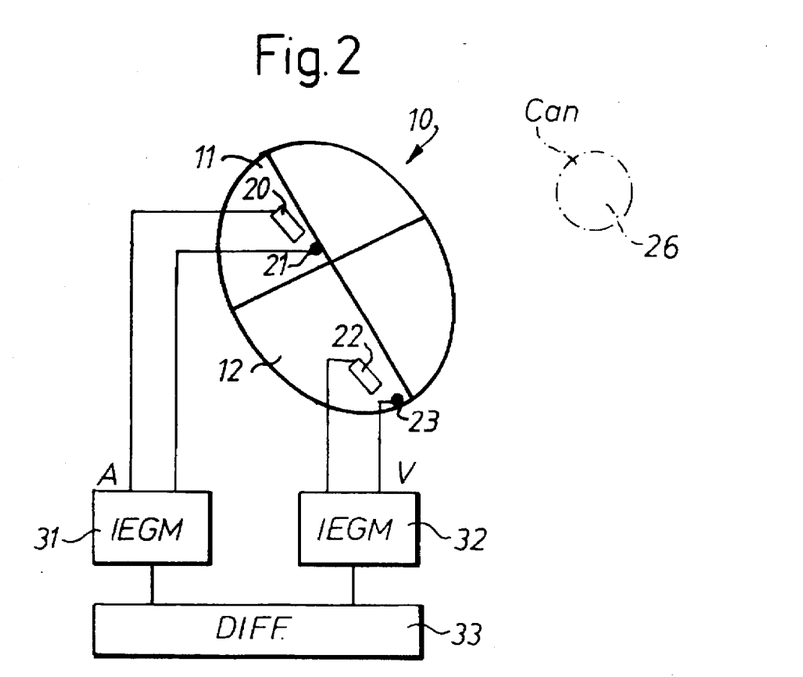
FIG. 2 is a schematic representation of an electrode configuration in a bipolar system, which may be used in accordance with the invention.

FIG. 2 shows another example of a known electrode configuration which may be used in accordance with the invention. FIG. 2 shows a heart 10 with two implanted bipolar electrodes, each having a tip electrode 21 and 23 and a ring electrode 20 and 22 in the atrium 11 and the ventricle 12, respectively. The atrial IEGM is then measured in the unit 31 between the ring and the tip of the bipolar electrode in the atrium 11 and the ventricular IEGM is measured in the unit 32 between the ring and the tip of the bipolar electrode in the ventricle 12. A differential IEGM can then be measured between the atrial and the ventricular IEGM:s in the unit 33. The can is indicated by the reference number 26.

Figure 3:
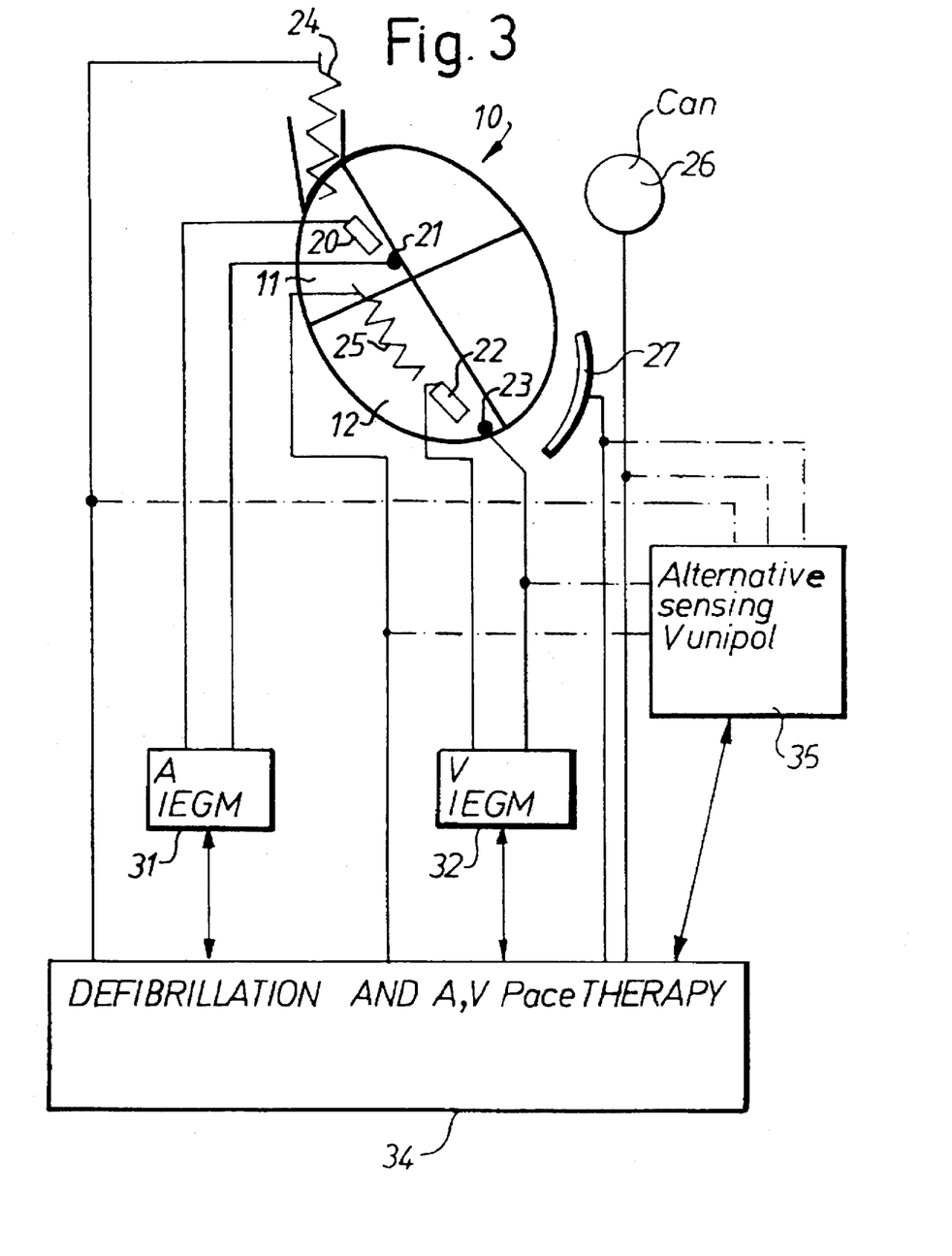
FIG. 3 is a schematic representation of an electrode configuration in a defibrillation stimulator, which may be used in accordance with the invention.

FIG. 3 shows a known electrode configuration in a defibrillation system, which may be used in accordance with the invention. FIG. 3 shows a heart 10 with two implanted bipolar electrodes, each having a tip electrode 21 and 23 and a ring electrode 20 and 22 in the atrium 11 and the ventricle 12, respectively. There are also two defibrillation electrodes 24 and 25 in the superior vena cava and the ventricle, respectively, and a patch extracardial electrode 27 and the can 26, which also may be another extracardially implanted electrode. The atrial IEGM is then measured in the monitoring unit 31 between the ring 20 and the tip 21 of the bipolar electrode in the atrium 11 and the ventricular IEGM is measured in the monitoring unit 32 between the ring 22 and the tip 23 of the bipolar electrode in the ventricle 12. The registration is bipolar. Alternatively, unipolar sensing in the ventricle may be carried out between the patch 27 and either of the tip electrodes 21 or 23, or either of the defibrillation electrodes 24 or 25. This system may be used for defibrillation and AV pacing therapy.

These examples shown in FIG. 1–3 are by no means exhaustive. Other electrode configurations may as well be used in these measurements.

Figure 4:
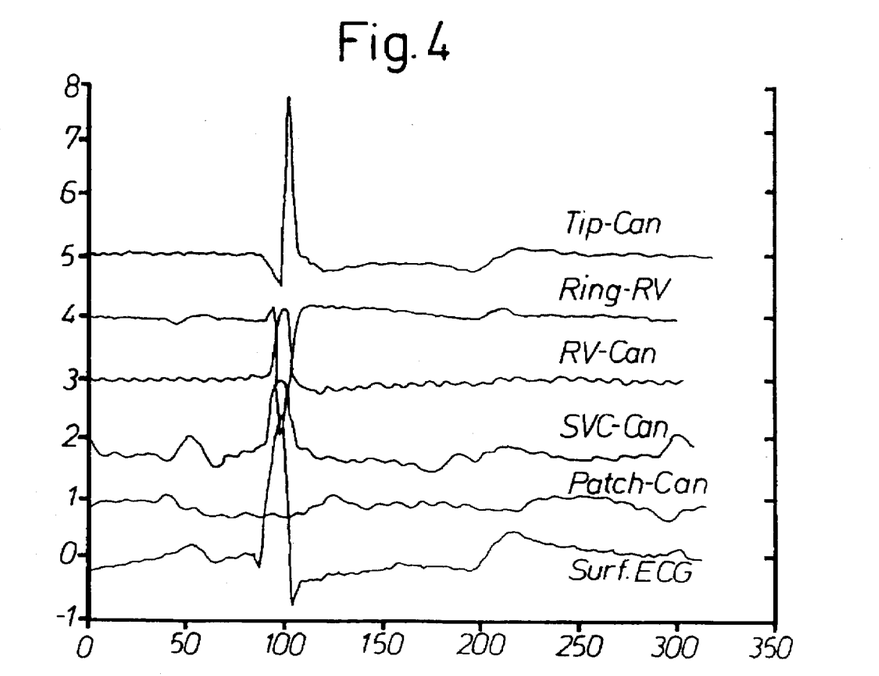
FIG. 4 shows recordings of the typical signals from groups of two implanted electrodes and a surface ECG.

In order to explain the invention a discussion follows below as to the appearance of the signals registered between pairs of implanted intracardiac electrodes. FIG. 4 shows recordings of signals registered between:

a. Tip (V)—Can b. Ring—RV (Defibrillation electrode right ventricle)

c. RV—Can d. SVC (Superior Vena Cava)—Can e. Patch—Can

A surface ECG (using limb leads) is also shown in FIG. 4. Signals a–e have been filtered (transformed) to remove effects from activities in the proximity of the electrodes.

From FIG. 4 can be seen that different characteristics from the different recorded IEGMs can be recognized in the surface ECG. The surface ECG thus is one form of a summation of the electrical activity in the heart. Of course the local phenomena at each electrode site will influence the signal registered by that electrode and prevail over influences from places farther away from the actual electrode site.

Figure 5A:
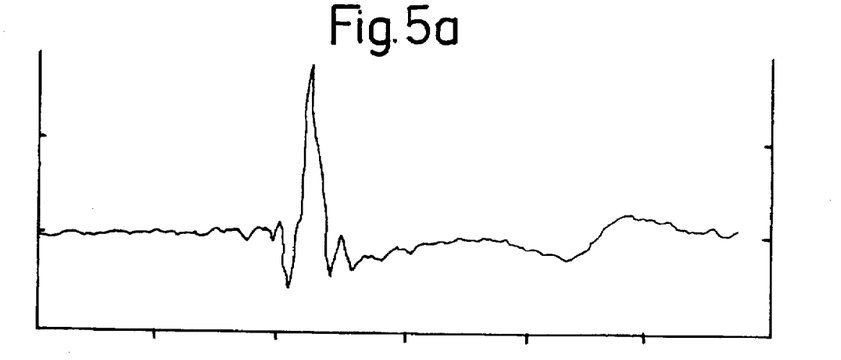
FIG. 5a shows recordings of the signals measured between tip electrode in the right ventricle and the can, i.e. the stimulator case, before application of the transfer function in accordance with the invention.
Figure 5B:
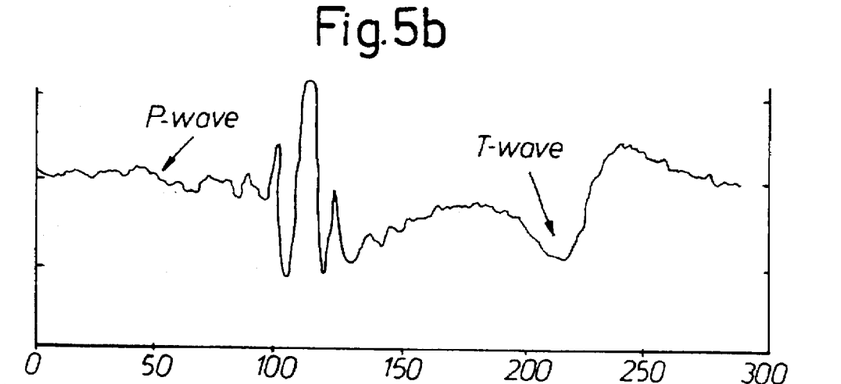

FIG. 5a shows the recordings of the unprocessed signals registered between tip (V) and can and FIG. 5b shows the influence of non-linear amplification which lessens the influence or even eliminates the local phenomena, in which one is not interested in this specific application according to the invention. This non-linear amplification will lead to smaller details becoming visible in the signal, i.e. details that have no local character but which describe the total functioning of the heart. In this case the signals have been filtered/transformed or blocked in order to remove the local influence on the signals before the summation of the signals. As may be noted, the P-wave is emphasized by the non-linear amplification. The T-wave is also emphasized in the same manner as is indicated in the FIG. 5. The non-linear amplification, using a transfer function, is discussed below.

It may of course be possible to filter/transform the signals at a later stage, if desired. This is further discussed in connection with FIGS. 13 and 14 below.

Figure 6:
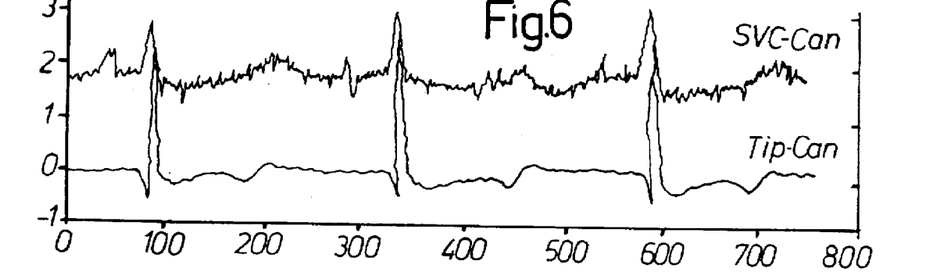
FIG. 6 shows two IEGM recordings SVC-CAN, TIP-CAN.

FIG. 6 shows the signal registered between the SVC (superior vena cava) and the Can, and the signals registered between the Tip and the Can.

Figure 7:
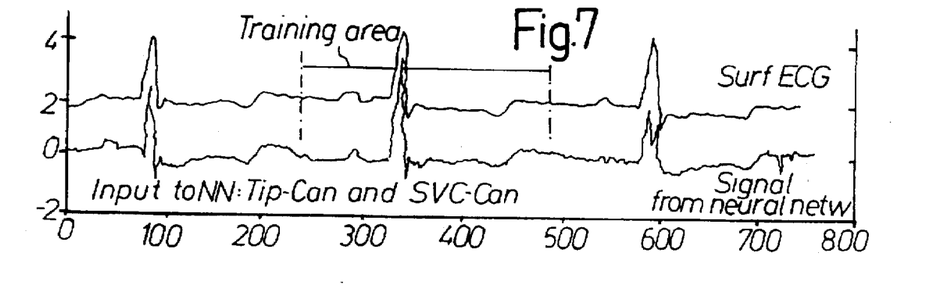
FIG. 7 shows a synthesized ECG from ((SVC-CAN)+(TIP-CAN)) and a surface ECG in accordance with the invention.

FIG. 7 shows the synthesized signals after processing, in a neural network, the signals shown in FIG. 6. The signals in FIG. 6 are used as input signals to a neural network. In practice a range of a surface ECG is chosen (e.g. one heart beat interval) and is compared in iterations with the weighted input signals. Once the neural network is "trained" on the chosen interval, the weights and parameters are "frozen" to be used subsequently. The surface ECG used in the training of the network is obtained from the patient in this method, but not necessarily a surface-ECG taken at the same time, but one of an earlier date.

If there is a significant essential change in the appearance of the patient's ECG, a new surface-ECG-recording should take place and that recording should be used instead. The parameters are then adjusted in iterations to make the combined signal reassemble the new surface ECG and after a number of iterations in the chosen range the specific details of an ordinary ECG will evolve out of the information entered into the neural network. This process must be understood such that the inherent characteristics in the signals are brought forward when adjusting the parameters applied to the separate signals before the summation. More about the method as such follows below in connection with the description of FIG. 15.

It should be clear that the inventive method include IEGM recordings obtained from paired connected implanted electrodes such as SVC and Can, Tip and Can, RV and Can etc. All signals are, according to the method, measured between two poles (groups of interconnected electrodes). Each group is either a single electrode: SVC, RV, Tip, Ring, Can or at least two electrically connected electrodes.

Figure 8:
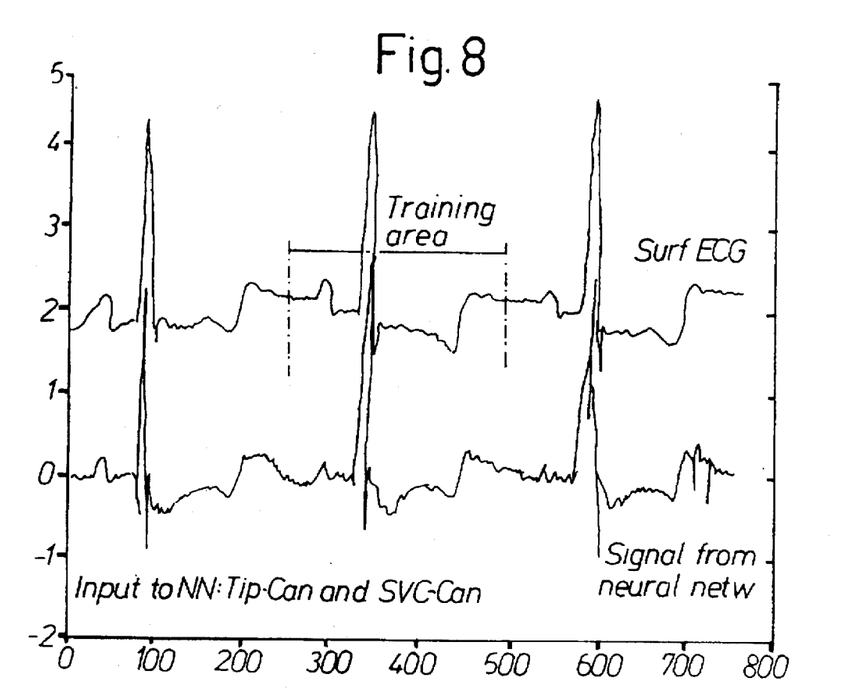
FIG. 8 is an enlargement of the diagram in FIG. 7.

FIG. 8 shows an enlargement of the diagram in FIG. 7, showing the training area in greater detail.

Figure 9:
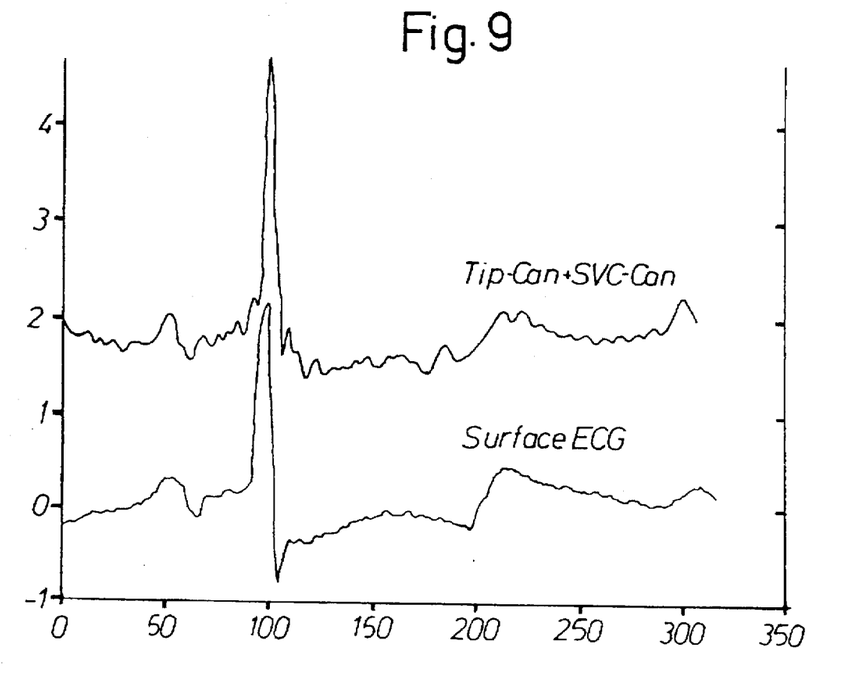
FIG. 9 shows recordings of respective signals between two groups of unprocessed interconnected electrodes (tip+can) and (SVC can) and a conventional surface ECG.

FIG. 9 shows the signal resulting from measuring between unprocessed interconnected electrodes Tip(V)+Can and SVC(Superior Vena Cava)+Can after signal processing in accordance with the invention, and below shows a surface ECG. One can see the close resemblance between the two signals. This is just one of many possible electrode combinations according to this invention.

Figure 10:
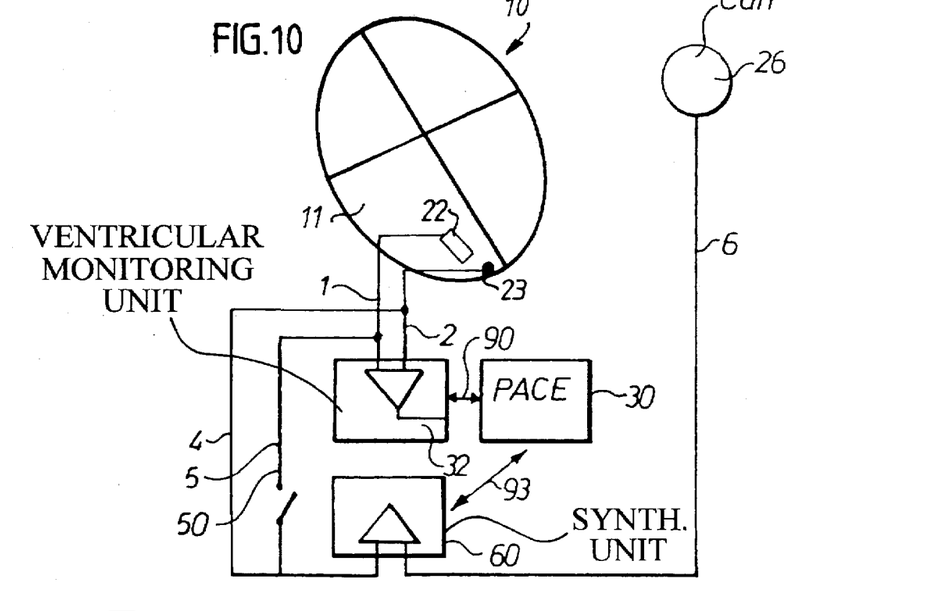
FIG. 10 shows a first embodiment of a heart stimulator system according to the invention.

FIG. 10 shows a first embodiment of an inventive implanted heart stimulator having two electrodes, namely a ring electrode 22 and a tip electrode 23, implanted in the right ventricle 11 of a heart 10. Conductors 1 and 2 from the electrodes 22 and 23, respectively, are connected to input terminals of a ventricular monitoring unit 32. The output signal from the unit 32 is a ventricular IEGM. The ventricular IEGM is then used, e.g., for controlling the pacing executed by the active implant 30. This part of the active implanted system corresponds to the usual setup for pacing. Conductors 4 and 5 connected to the electrodes 23 and 22, respectively are also connected to the input side of a synthesizing unit 60. The conductors 4 and 5 may be physically (electrically) connected to each other before the input terminal of the unit 60, or they may be processed in the unit 60 as will be discussed later. In one of the conductors 4 or 5, a switch 50 is arranged. Connection of the switch 50 and the action of unit 60 can be implemented in a multiplex mode. This is also true in the embodiments below. FIG. 10 also shows a can electrode 26, which may be the active implant case. This electrode 22 is also connected via a conductor 6 to the input side of the same unit 24.

According to the invention the signals received from the ring electrode 22 and the tip electrode 23, or from the ring electrode 22 only, are combined, such as by addition, in the synthesizing unit 60. The switch 50 may be controlled either to let the signal from the ring electrode 22 pass to the synthesizing unit 60, or not. The signal measured at the can electrode 26 is also fed to the synthesizing unit 60 and in the same way is added to the synthesized signal in unit 60. This provides the synthesized ECG according to the invention.

The reason for adding the signals from the electrodes 22 and 23 is that they will simulate a signal obtained from a bigger electrode. This is of course true for all possible electrode combinations forming a group in the sense of this invention.

A connection between the synthesizing unit 60 and the active implant 30 in the form of a double arrow 93 is shown to indicate the possibility of controlling the active implant in accordance with the information received from the synthesized ECG. Such an arrow 90 is also shown between the ventricular monitoring unit 32 and the active implant 30 to indicate the existing possibilities for controlling the active implant 30, however, the arrangement for stimulating the heart from the active implant 30 is not shown exactly in the drawing. This is a well known technique within the art.

The embodiment shown in FIG. 10 may of course include other electrodes implanted intra- and/or extracardially, and also the combination of signals may be between two electrodes and the Can as shown or between the Can and 3 or 4 implanted electrodes, respectively. The minimum requirement is the combination of signals from two electrodes, and this does not necessarily include the Can.

Figure 11:
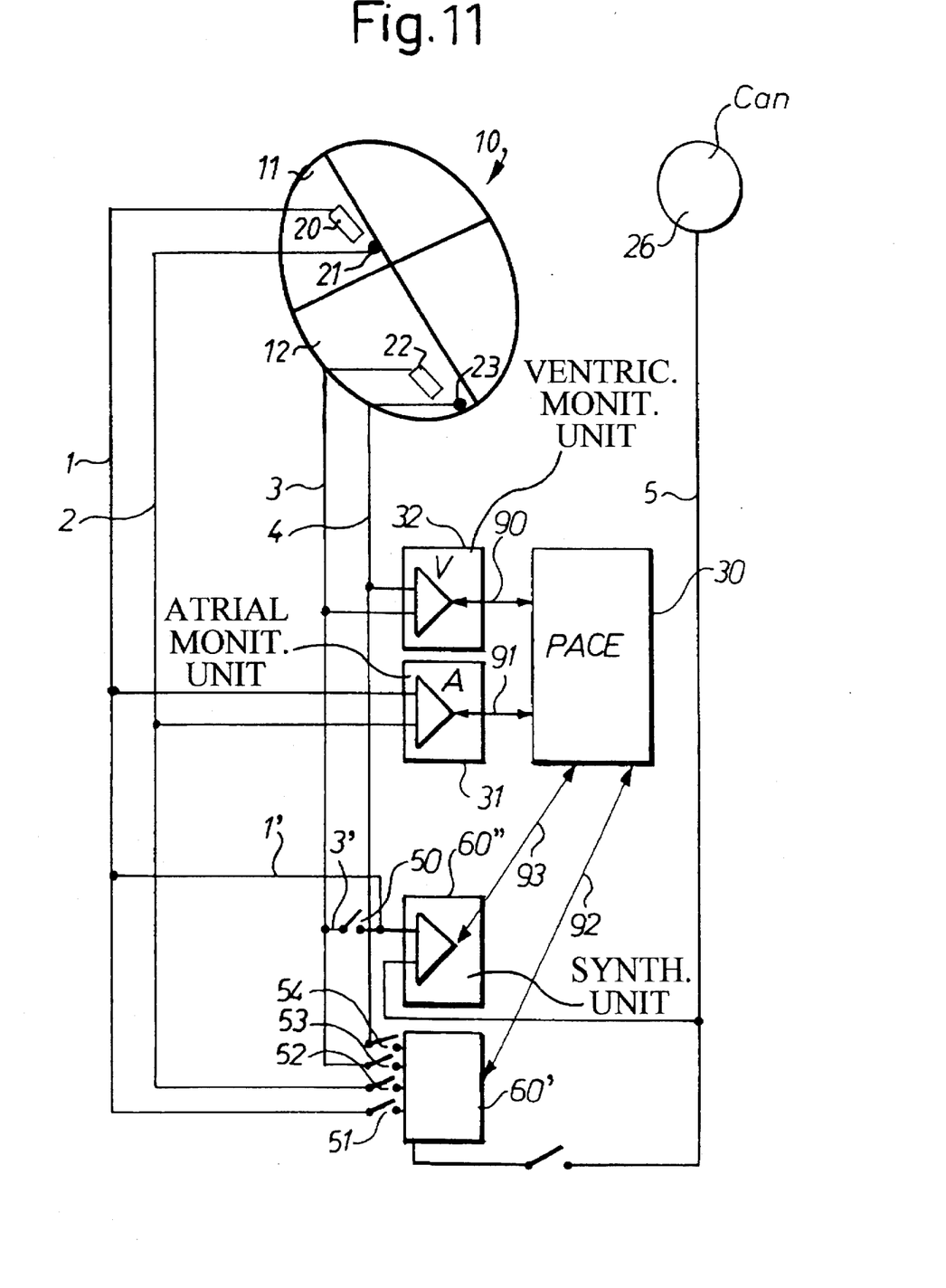
FIG. 11 shows a second embodiment of a heart stimulator according to the invention.

Another embodiment of the heart stimulation system according to the invention is shown in FIG. 11 in which an active implant has four electrodes: a ring electrode 20 and a tip electrode 21 implanted in the right atrium 11, and a ring electrode 22 and a tip electrode 2') implanted in the right ventricle 12, of a heart 10. The ring electrode 22 and the tip electrode 23 are connected via conductors 3 and 4, respectively, to the input of a ventricular monitoring unit 32. A ventricular IEGM may be measured in the ventricular monitoring unit 32. The ring electrode 20 and the tip electrode 21 are connected via conductors 1 and 2, respectively, to an atrial monitoring unit 31. An atrial IEGM may be measured in the atrial monitoring unit 31. The measured IEGM is then used for controlling the pacing executed by the active implant 30, which is indicated in the drawing by double arrows 90 and 91. This part of the active implant system corresponds to the usual setup for pacing.

FIG. 11 also shows a can electrode 26, which may be the active implant case.

FIG. 11 shows how to register synthesized or interconnected ECGs in two synthesizing units 60' and 60". The intracardiac electrodes 20, 21, 22 and 23 are also connected via respective conductors 1, 2, 3 and 4 to the input side of the unit 60'. Switches 51, 52, 53 and 54 are provided in the conductors 1, 2, 3 and 4 in order to connect or disconnect the electrodes 20, 21, 22 and 23 to or from the input terminal of the unit 60'. The can electrode 26 is connected via conductors 5 to the input side of the unit 60'. The can electrode 26 is also connected via conductor 5 to the input terminal of the synthesizing unit 60" as are the two ring electrodes 20 and 22 via conductors 1' and 3', respectively. In the same manner as above, a switch 50 is provided in the conductor 3'. The switches 50, 51, 52, 53 and 54 are provided to let the signals from the electrodes pass to the synthesizing units 60' and 60" or not, respectively.

The signal processing in units 60' and 60" will then provide the synthesized ECGs according to the invention. Connections in the form of double arrows 92 and 93 between the synthesizing units 60' and 60", respectively, and the active implant 20 are shown so as to indicate the possibility of controlling the active implant in accordance with the information received from the synthesized ECG.

Figure 12:
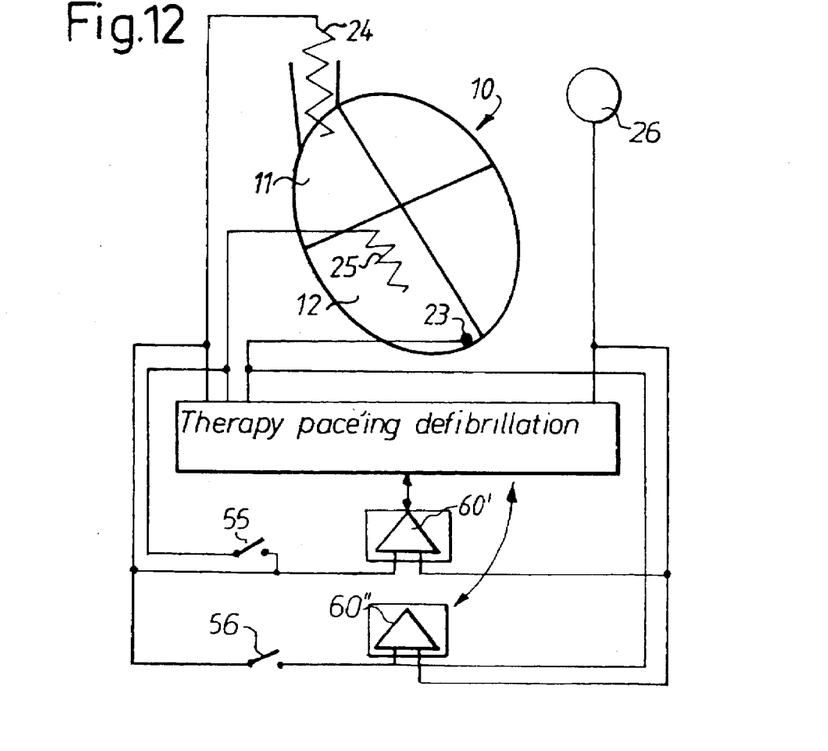
FIG. 12 shows a third embodiment of a heart stimulator according to the invention.

Another embodiment is shown in FIG. 12. In the heart 10 a defibrillation electrode 24 is implanted in the superior vena cava and another defibrillation electrode 25, in the right ventricle 12 and a tip electrode 22. This embodiment also includes an electrode 26 formed by the can. The electrodes are all connected via conductors to the active implant for pacing and defibrillation as is usual. Also shown is the possibility of registering an synthesized ECG in the atrial and ventricular monitoring units 60' and 60", respectively and also the possibility of choosing which signals to use in the processing by closing or opening switches 55 and/or 56. Units 60' and 60" are described in connection with FIG. 11. The difference from the other embodiments is primarily in the use of the defibrillation electrodes. This means that the active implant in this embodiment can be used for sensing cardiac events, for pacing in a normal manner, and for detection of anomalies in the behavior of the heart which will necessitate defibrillation. The synthesized ECG may in this embodiment, as in the other possible embodiments according to this invention, provide information to be used by the active implant for providing specific actions depending on the behavior of the heart.

Figure 13:
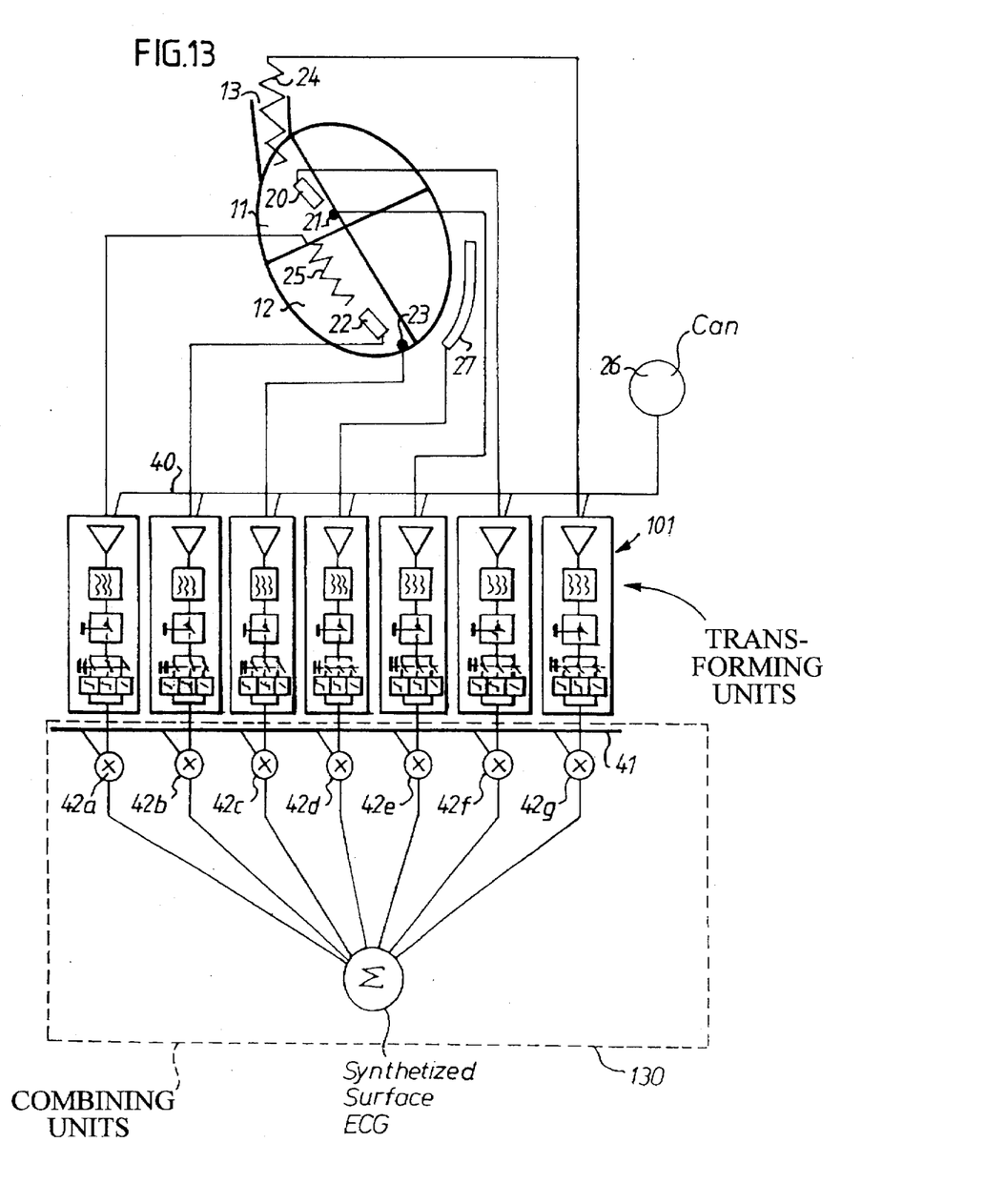
FIG. 13 shows a system according to the invention for registering and processing of signals from implanted electrodes.

FIG. 13 shows a schematic presentation of a heart 10, having a right atrium 11 and a right ventricle 12. A system having five intracardiac electrodes is shown implanted in the heart 10: a ring electrode 20 and a tip electrode 21 in the atrium 11 and a ring electrode 22 and a tip electrode 23 in the ventricle 12 and a defibrillation electrode 25. The system also includes a patch electrode 27 in contact with the outside of the heart. A defibrillation electrode 24 is placed near the location where the superior vena cava 13 enters the right atrium. The system also includes a can electrode 26.

Each of the above electrodes is connected to the input side of one of a number of transforming units 101. It is possible for the transforming units 101 to operate using a virtual (floating) ground as reference. Alternatively, any of the above electrodes can be selected as a reference electrode, the can electrode 26 being used in the embodiment shown in FIG. 13. In the embodiment shown in FIG. 13, the can electrode 26 is shown as being connected to the input side of each of the transforming units 101 via line 40. This connection could, however, alternatively be accomplished by switching means, which can also provide the capability of measuring signals across different selected pairs of electrodes. The respective outputs of the transforming units 101 are supplied to a series of multipliers 42a through 42g in a combining unit 130. Each multiplier 42a through 42g receives a signal setting its multiplying factor from a control bus 41. The signals which set the weighting factors in the multipliers 42a through 42g may be respectively coded so that the multipliers 42a through 42g are each set with an individual, appropriate weighting factor.

The outputs of the multipliers 42a through 42g are all supplied to a summation stage in the combining unit 130, the output of which constitutes the synthesized surface ECG.

Using the system shown schematically in FIG. 13, it is possible to register and/or process signals from two or more electrodes.

Figure 14:
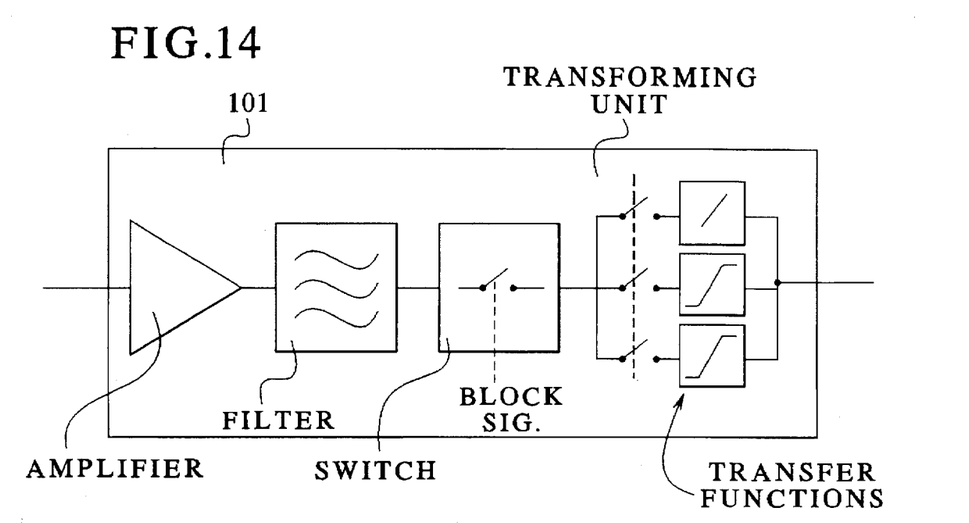
FIG. 14 shows an enlargement of the transforming unit, part of the system depicted in FIG. 13.

FIG. 14 shows an enlargement of the transforming unit in the diagram in FIG. 13, i.e. the unit 101.

The intracorporal signals from two or more electrodes will be amplified, filtered and possibly blocked during certain time intervals. This may be done by conventional means using well know techniques within the art, such as by using thresholds, or windows restricting either the amplitudes or the frequency of the signals received. The blocking of the signals may be individual at predetermined and controllable time intervals, so that the particular signal is prevented from affecting the result at the chosen time intervals. This signal processing will result in pre-treated second signals.

These individually processed second signals from two or more electrodes may then be summed and once more signal processed in a second processing procedure according to the invention.

Below the schematic illustration of the heart 10, FIG. 13 shows a schematic drawing of the principle according to which the inventive signal processing is carried out. First the received signals will pass through filtering/transforming and blocking circuitry in the respective transforming units 101. As noted above, the measured signals can be obtained across two selected electrodes, each transforming unit 101 may operate using a virtual (floating) ground as reference. Each transforming unit 101 includes one or more amplifiers, filters, blocking and transfer functions. The reason for this first processing is that the intracardiac electrodes will each pick up information as to the electrical activity resulting from cardiac activity in the proximity of the electrode, but also will pick up activity in other parts of the heart. The electrical activity induced in the very near proximity of each electrode will of course give a considerably greater contribution to the signal than activity occurring comparatively farther away.

The processed signals will then be fed to a second signal processing unit, referred to as a combining unit 130, for the summation, including weighting of the individual signals and processing to generate the synthesized surface ECG. The individual weighting takes place in the multipliers 42a–42g, wherein the output of the circuits 101 are respectively multiplied by different weights (scaling factors). The weights are respectively set via the control bus 41 which is connected to all of the multipliers.

Electrodes having a large surface and positioned extracardially normally give signals better suited for synthesizing a surface ECG. The signals from intracardiac and extracardiac electrodes can be used for mathematical processing by signal processing. The signals will thus be processed in order to filter out, e.g., high frequency components which mostly are the result of local (close proximity) electrical activity. This filtering effect can be accomplished in a more subtle fashion by blocking the signal during a given time period. Such a circuit can, e.g., be realized by circuitry which detects the fast slope of the IEGM from a passing wavefront of electrical activity at an early stage, thereby blocking most of the locally produced signal.

Figure 17A:
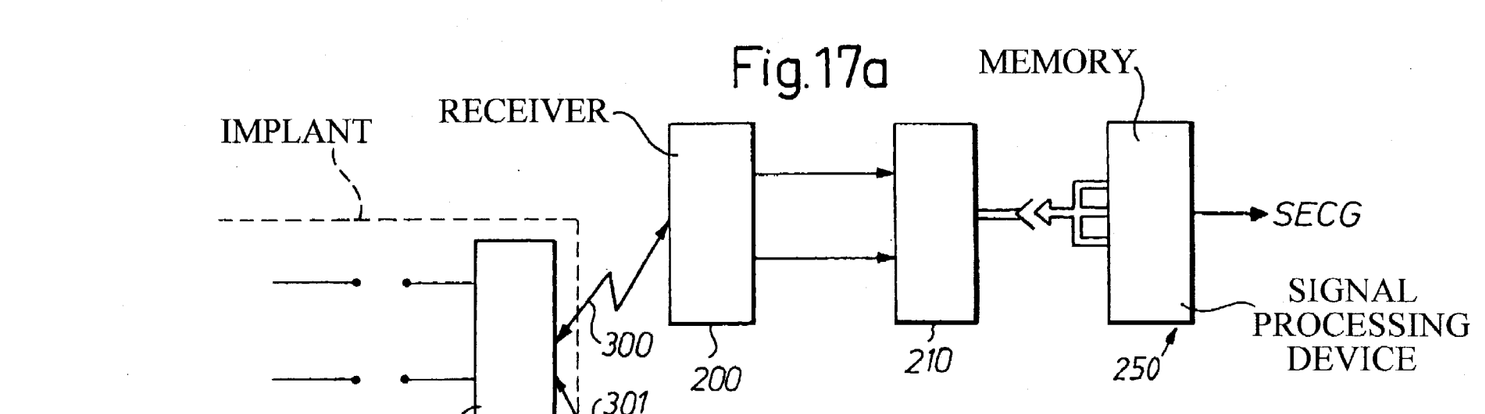
FIGS. 17a and 17b respectively show two further embodiments of a diagnostic device according to the invention.

If a small delay in the actual viewing of the signals, i.e. the synthesized surface ECG, can be tolerated, the result of the signal processing may be improved even more. If the signal first is stored, then mathematical processing may be done with a slight time delay, which will give time to remove the stored EEGM for that electrode (i.e. the part that originates locally such as the contribution from electrical activity in the close proximity of the electrode). The part that is removed may then be substituted by interpolation. The stored signal will then, according to the invention, be used instead of the directly-obtained signal for the filtering, blocking and multiplication by constants in the second processing procedure with the other intracoporal signals according to FIG. 13. This is shown in FIG. 17a.

During the processing each signal will be multiplied by a constant. This is done in order to favor signals which contain more far field ECG signals.

Still another improvement is the exaggerating of low amplitude signals like the P-wave in comparison with a QRS-complex. This may be done in the block designated "hear and non-linear transfer functions" in FIGS. 13 and 14 and FIG. 5b. Amplitudes outside specified limits may be clipped or gradually limited by a sigmoidal transfer function.

One way of implementing the signal processing is to use a neural network. The principle of such a technique will be shortly described herein with reference to FIG. 15. A thorough description of a neural network and its use is disclosed in the book "Neural Networks, a comprehensive foundation" by Simon Haykin, Macmillan College Publishing Company, ISBN 0-02352761-'7.

A neural network has several input signals and one or more output signals. Each input signal is processed and combined with the other weighted input signals. The combination of the signals are further processed in order to produce one or more output signals. The processing of the signals contains multiplication, addition and non-linear signal handling. A neural network may have different structures. This structure must first be selected. The neural network then has a number of hidden parameters (weights and biases). A characteristic of the neural network is that it must learn how to adjust these parameters. The learning action is performed on short, but sufficiently long and representative, input signal intervals which are fed into the neural network in order to produce an output signal, which will be compared with a reference signal. The learning procedure is performed by repeatedly feeding these input signals to the neural network and adjusting each parameter so that finally the output signal from the neural network resembles the reference signal. The neural network is now adjusted. New input signals will then produce output signals, which will be similar to the signals that the process, which the neural network is simulating, will produce.

Figure 15:
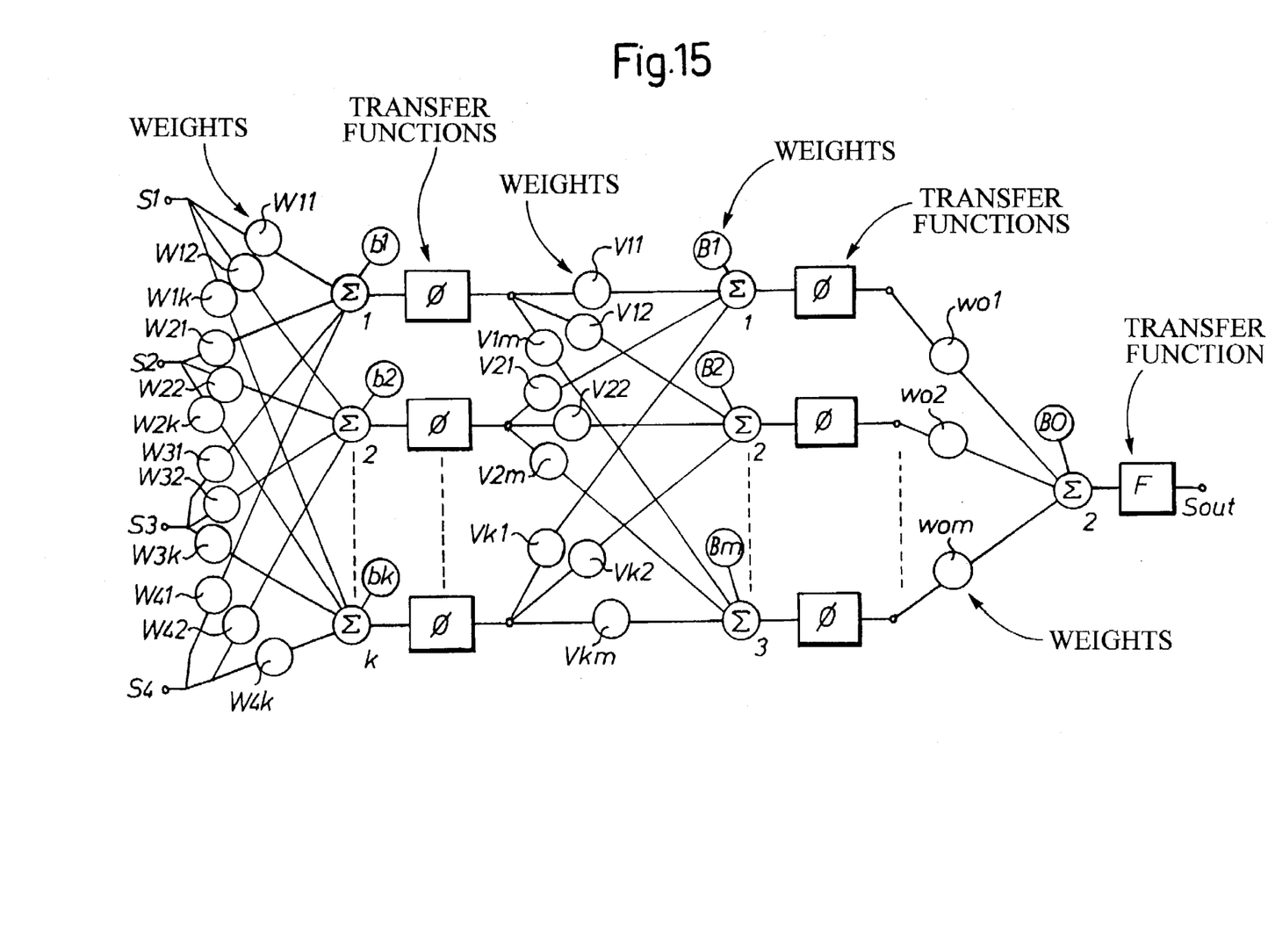
FIG. 15 is a schematic drawing of one version for implementing a neural network for signal processing in accordance with the invention.

The interior of the neural network will now be described in conjunction with FIG. 15. The input signals are S1, S2, S3 and S4. Each input signal is then multiplied by a certain weight (w11 to w4k). For every input signal there is as many weights as summing junctions. In FIG. 15 there are k summing junctions. In the summing junction all weighted signals and a bias signal are added. The bias signal is just a constant voltage. The output signal from the summing junctions passes a transfer function, denoted "φ". Very often this transfer function is a non-linear function, like the sigmoid function. In the same way as the input signals are processed, the output signals from the transfer function blocks are now handled, but with new weights, v11 to vkm, B1 to Bm. FIG. 15 shows only a single output, Sout. The transfer function is denoted "F". Normally this last transfer function is a linear function.

In the invention Sout is the synthesized surface ECG and the input signals are the intracardiac and/or intrathoracic signals, which contain information about the electrical activity of the heart.

A similar way to implement this invention is to use fuzzy logic instead of a neural network. There are similarities between a neural network and fuzzy logic. Because of this reason software exists that can transform a neural network into an electronic circuit utilizing a fuzzy logic technique.

The invention may be implemented in several ways. The signal processing may take place in a diagnostic device incorporated in the active implant as an integral part thereof or it may take place out of the active implant. The active implant may also have a transmitter for transmitting the synthesized ECG extracorporeally via telemetry. Such a transmitter may be a combined transmitter/receiver or the type of telemetric unit usually provided in active implants.

Figure 16:
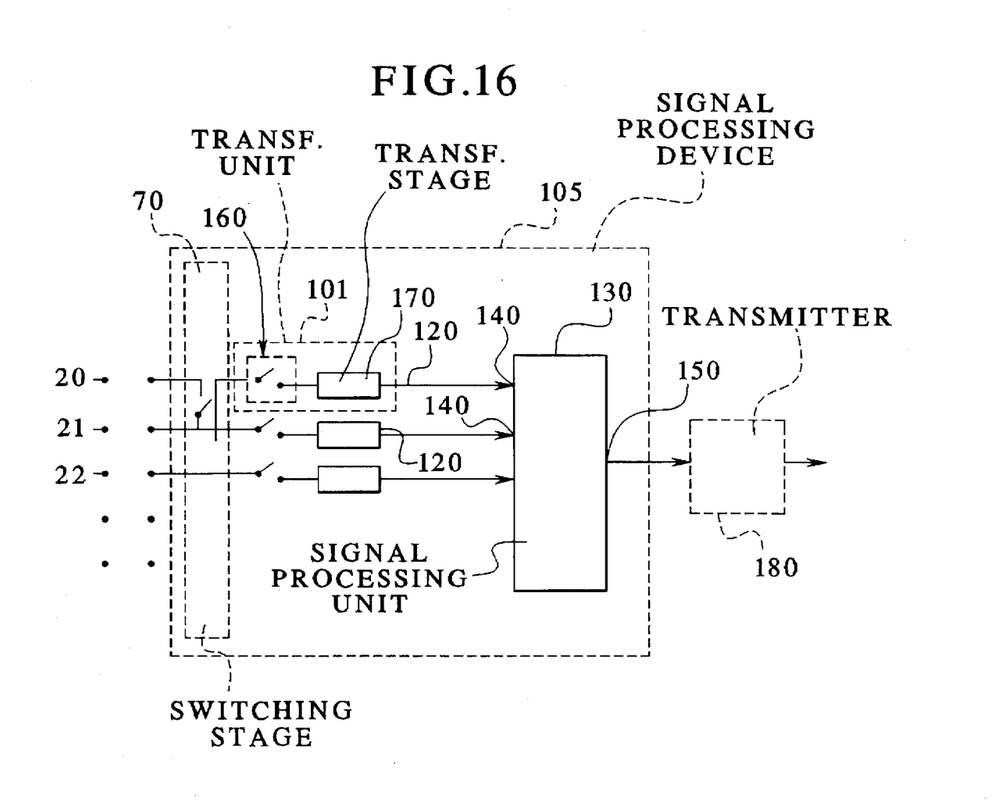
FIG. 16 shows a first embodiment of a diagnostic device according to the invention.

FIG. 16 shows the outputs from the implantable electrodes 20, 21, 22 . . . 30 and the corresponding inputs 110 to a signal processing device 105. The signal processing device 105 includes a controllable switching stage 160 and a transforming stage 170 in a transforming unit 101, with one such unit for each input 110. Each transforming unit 101 may also include e.g. an amplification stage. Each transforming unit 101 is also provided with an output 120. A second signal processing unit 130 is also shown having inputs 140 and an output 150. Several outputs may of course be provided. Connected to the signal processing device 105 is a transmitter 180 for transmitting the signals processed in the device 105.

The diagnostic device also includes a switching stage schematically shown at 70 for selective interconnection of the input signals from one or more electrodes before the signal processing units 101. These switches may be connected/disconnected in a multiplexing mode in order to facilitate the operating of the active implant, since when short circuiting two or more of the intracardiac electrodes this win affect the pacing/stimulating arrangement in the active implant in which the device according to the invention, or part of the device according to the invention, is included.

Figure 17B:
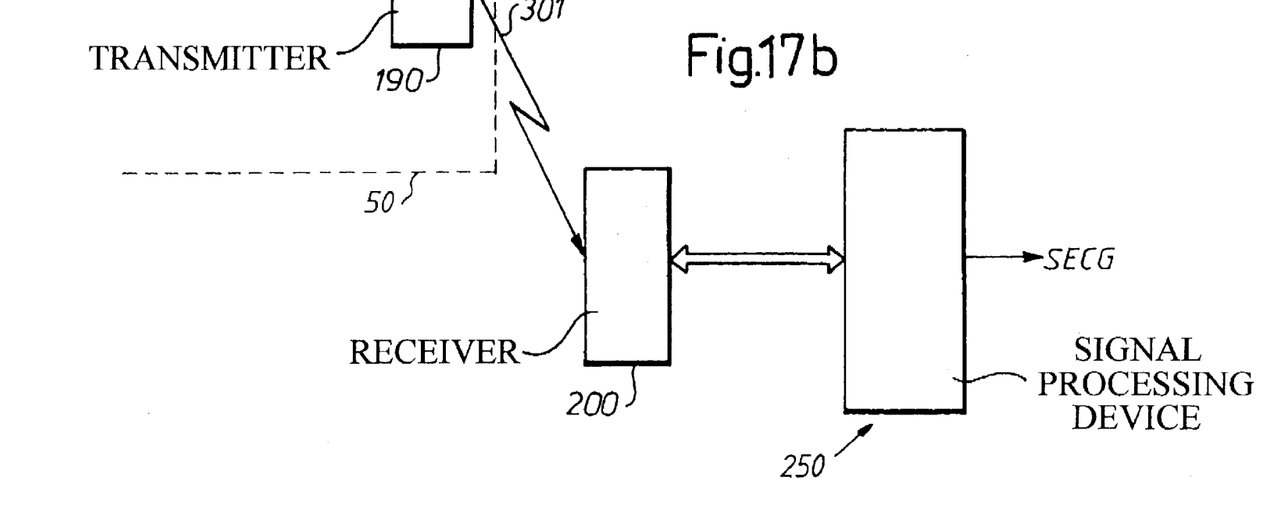

FIGS. 17 and 17b show another embodiment of the device according to the invention having outputs from the implantable electrodes 20, 21, 22, . . . 30. A transmitter 190 for receiving the signals from the electrodes is also included. This part of the device is placed in an active implant.

The transmitter 190 is arranged to transmit the signals from the implantable electrodes and two pathways 300 and 301 are shown in order to illustrate two other embodiments of the device according to the invention. Actually there need only be one pathway in each embodiment. After the pathway 300 there is a receiver 200 and, in the first embodiment of FIG. 17a, a memory unit 210 for storing the signals until a later time. The memory unit 210 is connectable via a data bus to a processing unit 105. It should be understood in this document that a radio receiver and a radio transmitter are merely examples of a type of receiver and a transmitter. The signals could just as well be transmitted by any method which is well known in the art.

In the second embodiment shown in FIG. 17b, the receiver 200 is connected to a signal processing device 105 according to the invention.

In these three last embodiments of the invention, it is of course possible to send the unprocessed signals or the processed signals at one stage or the other via the public telephone network to a location where the synthesized ECG-signal may be viewed and evaluated.

The memory unit for storing may also be situated in the active implant. The active implant will also contain components usually provided in an active implant, such as pacing and/or defibrillation circuitry etc.

The sensors or electrodes which are used in the context of the invention can include, as noted above, electrodes for measuring IEGMs, impedance sensors, blood pressure sensors, physical activity sensors, position sensors and other suitable sensors known to those of ordinary skill in the art.

Although the invention has been described with respect to particular embodiments, it is to be understood that these embodiments are merely illustrative to the application of the principles of the invention. Numerous modifications may be made therein and other arrangements may be devised without departing from the spirit and scope of the invention.

We claim as our invention:

1. A physiological signal processing device comprising:
   a plurality of pairs of physiological sensors adapted for in vivo implantation in a subject, each pair of physiological sensors respectively generating an IEGM signal;
   a plurality of first signal processing units, each first signal processing unit having an input for receiving at least one of said IEGM signals, and an output;
   a second signal processing unit having a plurality of inputs respectively connected to said outputs of said first signal processing units, and having an output;
   each of said first signal processing units comprising means for subjecting at least one of said IEGM signals, supplied at its input, to at least one transfer function for producing a pre-treated signal at its output; and
   said second signal processing unit comprising means for combining at least two of said pre-treated signals for producing at least one synthesized ECG signal at said output of said second signal processing unit.

2. A physiological signal processing device as claimed in claim 1 further comprising a plurality of switching means connected preceding an input of at least one of said first signal processing units for selectively combining at least two of said IEGM signals prior to said input of at least one of said first signal processing units.

3. A physiological signal processing device as claimed in claim 1 wherein each first signal processing unit includes a controllable switch for blocking the input for that first signal processing unit during a time interval selected by said controllable switch.

4. A physiological signal processing device as claimed in claim 1 wherein each first signal processing unit comprises a transforming stage, said transforming stage having said transfer function and operating on said input signal in accordance with said transfer function.

5. A physiological signal processing device as claimed in claim 4 wherein said transfer function stage comprises means for producing a linear transfer function, means for producing an upper and lower limited transfer function, and means for producing a sigmoid transfer function, and means for selecting one of said linear, limited or sigmoid transfer functions as said selected transfer function.

6. A physiological signal processing device as claimed in claim 1 further comprising transmitter means, connected to said output of said second signal processing unit, for transmitting said synthesized ECG signal to a location remote from said transmitter means.

7. A physiological signal processing device as claimed in claim 1 wherein said plurality of physiological sensors comprise a plurality of electrodes respectively adapted for implantation at a plurality of different cardiac sites.

8. A physiological signal processing device as claimed in claim 7 further comprising transmitter means, connected to each of said electrodes, for wirelessly transmitting the respective IEGM signals from said electrodes to said inputs of said first signal processing units at a location remote from said transmitter means.

9. A physiological signal processing device as claimed in claim 8 further comprising receiver means, disposed at said location remote from said transmitter means, for receiving the IEGM signals transmitted by said transmitter means and forwarding said IEGM signals to the inputs of said first signal processing units.

10. A physiological signal processing device as claimed in claim 9 further comprising memory means, connected to said receiver means, for storing said IEGM signals.

11. A physiological signal processing device as claimed in claim 10 further comprising a first housing adapted for implantation in said subject and containing said transmitter means, and a second, extracorporeal housing containing said receiver means and said memory means, and means for reading out said memory means for supplying said IEGM signals to said inputs of said first signal processing units.

12. A physiological signal processing device as claimed in claim 1 wherein said means for combining at least two of said pre-treated signals comprise means for adding at least two of said pre-treated signals.

13. A physiological signal processing device as claimed in claim 1 wherein said means for combining at least two of said pre-treated signals comprise means for combining said at least two of said pre-treated signals according to fuzzy logic.

14. A physiological signal processing device as claimed in claim 1 wherein said means for combining at least two of said pre-treated signals comprise a neural network.

15. A physiological signal processing device as claimed in claim 14 wherein said neural network comprises means for operating in a manually trained mode.

16. A physiological signal processing device as claimed in claim 14 wherein said neural network comprises means for operating in a self-learning mode.

17. A physiological signal processing device as claimed in claim 1 further comprising means for obtaining a surface ECG signal of said subject, and wherein said means for combining at least two of said pre-treated signals comprise means for storing said surface ECG signal and for producing a synthesized ECG signal matched to said surface ECG signal.

18. A method for physiological signal processing comprising the steps of:

obtaining a plurality of IEGM signals in vivo from a subject;

supplying at least one of said IEGM signals respectively to a plurality of first signal processing units;

in each of said first signal processing units, subjecting at least one of said IEGM signals to at least one transfer function for producing a pre-treated signal; and supplying said pre-treated signals to a second signal processing unit and, in said second signal processing unit, combining at least two of said pre-treated signals for producing at least one synthesized ECG signal.

19. A method as claimed in claim 18 comprising the additional step of:

selecting a time interval; and blocking said at least one of said measured physiological signals in at least one of said first signal processing units for said time interval.

20. A method as claimed in claim 18 comprising the additional step of:

in each of said first signal processing units, selecting said at least one transfer function from among the group of transfer functions comprising a linear transfer function, an upper and lower limited transfer function and a sigmoid transfer function.

21. A method as claimed in claim 18 wherein the step of combining at least two of said pre-treated signals comprises adding at least two of said pre-treated signals.

22. A method as claimed in claim 18 wherein the step of combining at least two of said pre-treated signals comprises combining at least two of said pre-treated signals according to fuzzy logic.

23. A method as claimed in claim 18 wherein said second unit comprises a neural network and comprising the additional step of obtaining a surface ECG signal from said subject, and wherein the step of combining at least two of said pre-treated signals comprises training said neural network to produce said at least one synthesized ECG signal matched to said surface ECG signal.

24. A method as claimed in claim 18 wherein the step of training said neural network comprises manually training said neural network.

25. A method as claimed in claim 18 wherein the step of training said neural network comprises operating said neural network in a self-learning mode.

* * * * *